(12) United States Patent
Kim

(10) Patent No.: US 10,948,346 B2
(45) Date of Patent: Mar. 16, 2021

(54) SPECTROMETER, APPARATUS AND METHOD FOR MEASURING BIOMETRIC INFORMATION

(71) Applicant: SAMSUNG ELECTRONICS CO., LTD., Suwon-si (KR)

(72) Inventor: Dong Ho Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 412 days.

(21) Appl. No.: 15/586,720

(22) Filed: May 4, 2017

(65) Prior Publication Data

US 2018/0128680 A1 May 10, 2018

(30) Foreign Application Priority Data

Nov. 8, 2016 (KR) ........................ 10-2016-0148207

(51) Int. Cl.
| | | |
|---|---|---|
| *G01J 3/10* | (2006.01) | |
| *G01J 3/44* | (2006.01) | |
| *G01J 3/32* | (2006.01) | |
| *A61B 5/145* | (2006.01) | |

(Continued)

(52) U.S. Cl.
CPC ............. *G01J 3/10* (2013.01); *A61B 5/1455* (2013.01); *A61B 5/14532* (2013.01); *A61B 5/14546* (2013.01); *G01J 3/28* (2013.01); *G01J 3/32* (2013.01); *G01J 3/44* (2013.01); *A61B 2560/0242* (2013.01);

(Continued)

(58) Field of Classification Search
CPC ........ G01J 3/10; G01J 3/32; G01J 3/44; G01J 2003/102; G01J 2003/106; G01J 2003/284; A61B 5/1455; A61B 5/14532; A61B 5/14546; A61B 2560/0242

See application file for complete search history.

(56) References Cited

U.S. PATENT DOCUMENTS 8,649,838 B2 * 2/2014 Chen .................. A61B 5/14551
 600/310
9,293,668 B2 3/2016 Do et al.
9,395,473 B2 * 7/2016 Choi, II ............... A61B 5/0075

(Continued)

FOREIGN PATENT DOCUMENTS

JP 5265050 B1 8/2013
KR 10-0735460 B1 7/2007

(Continued)

OTHER PUBLICATIONS

Szczecinski L, Morawski R Z and Barwicz A 1994 Original-domain Tikhonov regularisation and non-negativity constraint improve resolution of spectrometric analysis Proc. 13th IMEKO World Congress (Torino, Sep. 5-9, 1994) pp. 441-446 (Year: 1994).*

(Continued)

*Primary Examiner* — Daniel L Cerioni
*Assistant Examiner* — Raymond P Dulman
(74) *Attorney, Agent, or Firm* — Sughrue Mion, PLLC

(57) ABSTRACT

A spectrometer according to one aspect may include a plurality of light sources configured to emit light to a target object, a plurality of wavelength controllers installed on one surface of each of the plurality of light sources and configured to adjust a peak wavelength band of each of the light sources, and a detection unit configured to detect light returning from the target object.

17 Claims, 12 Drawing Sheets

(51) Int. Cl.
*A61B 5/1455* (2006.01)
*G01J 3/28* (2006.01)

(52) U.S. Cl.
CPC ... *G01J 2003/102* (2013.01); *G01J 2003/106* (2013.01); *G01J 2003/284* (2013.01)

(56) References Cited

U.S. PATENT DOCUMENTS

| | | | | |
|---|---|---|---|---|
| 2003/0176777 | A1* | 9/2003 | Muller-Dethlefs | A61B 5/14532 600/322 |
| 2007/0057902 | A1 | 3/2007 | Joung | |
| 2009/0086206 | A1* | 4/2009 | Mori | G01J 3/10 356/326 |
| 2010/0185068 | A1* | 7/2010 | Park | A61B 5/021 600/324 |
| 2011/0160555 | A1* | 6/2011 | Reifman | A61B 5/14532 600/365 |
| 2012/0059232 | A1* | 3/2012 | Gross | A61B 5/14532 600/316 |
| 2012/0129269 | A1* | 5/2012 | Choi, II | A61B 5/0075 436/164 |
| 2012/0197096 | A1 | 8/2012 | Ridder et al. | |
| 2012/0248985 | A1 | 10/2012 | Lin et al. | |
| 2014/0073892 | A1* | 3/2014 | Randloev | A61B 5/14532 600/365 |
| 2015/0157220 | A1* | 6/2015 | Fish | A61B 5/02055 600/301 |
| 2015/0219906 | A1* | 8/2015 | Maiwald | G02B 27/141 359/566 |
| 2015/0308958 | A1* | 10/2015 | Lemieux | G01J 3/443 435/287.2 |
| 2015/0309400 | A1* | 10/2015 | Kawamura et al. | G03B 21/2033 353/31 |
| 2016/0113530 | A1* | 4/2016 | Nagahiro | A61B 5/02416 600/473 |
| 2017/0067778 | A1* | 3/2017 | Sugi | A61B 5/14552 |
| 2017/0311897 | A1* | 11/2017 | Faccioli | A61B 5/0004 |

FOREIGN PATENT DOCUMENTS

| | | |
|---|---|---|
| KR | 10-0754010 B1 | 9/2007 |
| KR | 10-0861461 B1 | 10/2008 |
| KR | 10-0943966 B1 | 2/2010 |
| KR | 10-2014-0050396 A | 4/2014 |
| KR | 10-2014-0121338 A | 10/2014 |
| KR | 10-1490233 B1 | 2/2015 |
| KR | 10-1545309 B1 | 8/2015 |
| WO | 2010/082852 A1 | 7/2010 |
| WO | 2016191307 A1 | 12/2016 |

OTHER PUBLICATIONS

Communication dated Jan. 19, 2018, issued by the European Patent Office in counterpart European Application No. 17177277.5.

Yeh, et al., "A Low Cost LED Based Spectrometer", 2006, Journal of the Chinese Chemical Society, vol. 53, Issue No. 5, pp. 1,067-1,072.

Szymon Beczkowski et al., "LED Spectral and Power Characteristics Under Hybrid PWM/AM Dimming Strategy", Energy Conversion Congress and Exposition (ECCE), 2010 IEEE, IEEE, XP031787146, Piscataway, NJ, Sep. 12, 2010, pp. 731-735.

Steven Keeping et al., "LED Color Shift Under PWM Dimming", Digikey Electronics, XP055681159, Feb. 11, 2014, 7 pages, Retrieved from URL: <https://www.digikey.com/en/articles/led-color-shift-under-pwm-dimming>.

Communication dated Apr. 9, 2020, issued by the European Patent Office in counterpart European Application No. 17 177 277.5.

\* cited by examiner

SPECTROMETER, APPARATUS AND METHOD FOR MEASURING BIOMETRIC INFORMATION

CROSS-REFERENCE TO RELATED APPLICATION(S)

This application claims the benefit of Korean Patent Application No. 10-2016-0148207, filed on Nov. 8, 2016, in the Korean Intellectual Property Office, the entire disclosure of which is incorporated herein by reference for all purposes.

BACKGROUND

1. Field

The following description relates to a spectrometer and an apparatus and method for measuring biometric information using the spectrometer.

2. Description of Related Art

Recently, methods of non-invasively measuring biometric information, such as a blood sugar, using Raman spectroscopy or near-infrared (NIR) spectroscopy have been studied. Generally, a biometric information measurement instrument using spectroscopic techniques is composed of a light source for emitting light toward a target object and a detector for detecting an optical signal received from the target object. The biometric measurement instrument reconstructs a spectrum using the optical signal detected by the detector and measures biometric information such as a blood glucose level, cholesterol, calories, and the like, through analysis of skin near-infrared absorption spectrum or analysis of Raman scattered light. The general biometric information measurement instrument as described above acquires a spectrum using a broadband light source, such as a tungsten lamp, and a grating narrowband filter.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In one general aspect, there is a spectrometer including: a plurality of light sources configured to emit light to a target object; a plurality of wavelength controllers installed on one surface of each of the plurality of light sources and configured to adjust a peak wavelength band of each of the light sources; and a detection unit configured to detect light received from the target object.

Each of the plurality of wavelength controllers may include at least one of a resistance heating element and a thermoelectric element to adjust the temperature of each light source.

The spectrometer may further include a controller configured to control each of the plurality of light sources to emit light of a preset peak wavelength band by adjusting a temperature of each of the wavelength controllers corresponding to the respective light sources according to a temperature preset for each of the light sources.

The controller may control turn-on/off of the plurality of light sources in a time-division manner.

The controller may control the plurality of light sources according to a preset operating condition so that each of the plurality of light sources emits light of a wavelength different from the preset peak wavelength band.

The preset operating condition may include one or both of current intensity and pulse duration of each light source.

The spectrometer may further include a controller configured to reconstruct a spectrum based on an optical signal detected by the detection unit.

The controller may reconstruct the spectrum using a Tikhonov regularization method.

In another general aspect, there is provided an apparatus for measuring biometric information, the apparatus including: a main body; a light source unit being mounted in the main body and comprising a plurality of light sources configured to emit light to a target object and a plurality of wavelength controllers each of which is installed on one side of each of the plurality of light sources; a detection unit mounted in the main body and configured to detect light returning from the target object; and a controller mounted in the main body and configured to control a peak wavelength of each of the light sources corresponding to the wavelength controllers by controlling each of the plurality of wavelength controllers and to measure biometric information of the target object based on the detected light.

Each of the plurality of wavelength controllers may include at least one of a resistance heating element and a thermoelectric element to adjust the temperature of each light source.

The controller may include a temperature controller configured to control a temperature of each of the plurality of wavelength controller according to a temperature preset for each light source so that each light source emits light of a preset peak wavelength band to the target object when a request for measuring biometric information of a user is received.

The controller may include an operating controller configured to control turn on/off of the plurality of light sources based on a preset operating condition when a request for measuring biometric information of a user is received.

The preset operating condition may include one or both of current intensity and pulse duration of each light source.

The controller may include a signal processor configured to detect an optical signal detected by the detection unit and measure the biometric information by processing the received optical signal.

The signal processor may reconstruct a spectrum based on the received optical signal and measure the biometric information based on the reconstructed spectrum.

The signal processor may reconstruct the spectrum using a Tikhonov regularization method based on the received optical signal and an operating condition preset for each of the plurality of light sources.

The biometric information may include a blood glucose level, triglycerides, cholesterol, calories, protein, and uric acid.

The light source unit may further include a plurality of redirecting elements to adjust a direction of the light emitted from each of the plurality of light sources to be directed toward the target object.

The apparatus may further include a display configured to display a variety of information including the measured biometric information under a control of the controller.

The apparatus may further include a communicator configured to be communicatively connected to an external device under a control of the controller and transmit a variety of information including the measured biometric information.

In still another general aspect, there is provided a method of measuring biometric information, the method including: receiving a biometric information measurement command from a user; controlling each of a plurality of wavelength controllers corresponding to each of a plurality of light sources to adjust a peak wavelength of each light source; operating the plurality of light sources to emit light to a target object; detecting light returning from the target object using a detection unit; and measuring biometric information of the target object based on the detected light.

The adjusting of the peak wavelength may include controlling a temperature of each of the plurality of wavelength controllers according to a temperature preset for each of the light sources so that each light source emits light of a preset peak wavelength.

The emitting of the light may include controlling turn-on/off of the plurality of light sources in a time-division manner based on a preset operating condition.

The preset operating condition may be set for each of the plurality of light sources and may include one or both of current intensity and pulse duration of each light source.

The measuring of the biometric information may include reconstructing a spectrum based on the detected light and measuring the biometric information based on the reconstructed spectrum.

The method may further include displaying a variety of information including the measured biometric information to the user.

In an exemplary embodiment, there is a spectrometer including: a plurality of light sources configured to emit light toward a target object; a plurality of wavelength controllers disposed on surfaces of the plurality of light sources and configured to adjust peak wavelength bands of the plurality of light sources; and a detection unit configured to detect light received from the target object.

Further, one of the plurality of wavelength controllers includes at least one from among a resistance heating element and a thermoelectric element to adjust a temperature of one of the plurality of light sources.

There may additionally be a spectrometer controller configured to control the one of the plurality of light sources to emit light of a preset peak wavelength band by adjusting a temperature of the one of the plurality of wavelength controllers corresponding to the one of plurality of light sources, according to a temperature preset for the one of the plurality of light sources.

In another exemplary embodiment, there is an apparatus for measuring biometric information, the apparatus including: a main body; a light source unit disposed in the main body and including a plurality of light sources configured to emit light toward a target object and a plurality of wavelength controllers disposed on the plurality of light sources; a detection unit disposed in the main body and configured to detect light received from the target object; and a spectrometer controller disposed in the main body and configured to control a peak wavelengths of the plurality of light sources corresponding to the plurality of wavelength controllers by controlling the plurality of wavelength controllers and to measure biometric information of the target object based on the detected light.

One of the plurality of wavelength controllers may include at least one from among a resistance heating element and a thermoelectric element to adjust the temperature of one of plurality of light sources.

The spectrometer controller may include a temperature controller configured to control a temperature of the one of the plurality of wavelength controllers according to a temperature preset for the one of the plurality of light sources so that the one of the plurality of light sources emits light of a preset peak wavelength band to the target object when a request for measuring biometric information of a user is received.

In yet another exemplary embodiment, there is a method of measuring biometric information, the method including: receiving a biometric information measurement command from a user; controlling a plurality of wavelength controllers corresponding to a plurality of light sources to adjust peak wavelengths of the plurality of light sources; operating the plurality of light sources to emit light toward a target object; detecting light received from the target object using a detection unit; and measuring biometric information of the target object based on the detected light.

Other features and aspects will be apparent from the following detailed description, the drawings, and the claims.

Figure 1:
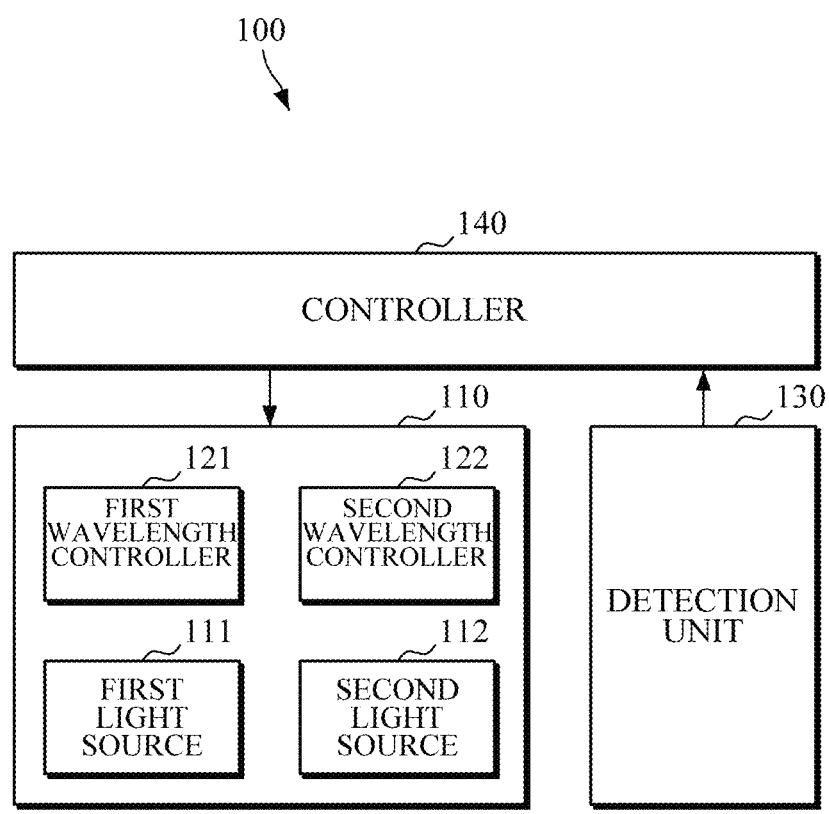
FIG. 1 is a block diagram illustrating a spectrometer according to one exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising", will be understood to imply the inclusion of stated elements but not the exclusion of any other elements. Terms such as " . . . unit" and "module" denote units that process at least one function or operation, and they may be implemented by using hardware, software, or a combination of hardware and software.

Hereinafter, exemplary embodiments of a spectrometer and an apparatus and method for measuring biometric information will be described in detail with reference to the accompanying drawings.

FIG. 1 is a block diagram illustrating a spectrometer according to one exemplary embodiment.

Referring to FIG. 1, the spectrometer 100 includes a light source unit 110, a detection unit 130, and a controller 140. In an exemplary embodiment, the controller 140 is a spectrometer controller and the light source unit 110, detection unit 130, and the controller 140 are all hardware components.

The light source unit 110 may include a plurality of light sources, i.e., a first light source 111 and a second light source 112, which emit light to a target object. The light source unit 110 is illustrated as including only two light sources, the first and the second light sources 111 and 112, but it is merely an example for convenience of description, and the number of light sources is not particularly limited. In this case, each of the plurality of light sources may include a light-emitting diode (LED), a laser diode, a phosphor material, and the like. In addition, each of the first and the second light sources 111 and 112 may be configured to emit laser single light or near-infrared light so as to use Raman spectroscopy or near infrared spectroscopy.

In addition, the light source unit 110 may further include a plurality of wavelength controllers, i.e., a first wavelength controller 121 and a second wavelength controller 122. Each of the plurality of wavelength controllers are disposed on one side of the corresponding light source to individually control a peak wavelength band of each light source. For example, the first wavelength controller 121 is disposed, e.g., installed or mounted, to one side of the first light source 111 and the second wavelength controller 122 is disposed e.g., installed or mounted, to one side of the second light source 112. A number of wavelength controllers is not limited to two, and a matching number or a corresponding number of wavelength controllers may be provided for a number of light sources to individually control the peak wavelength emitted from each of the first and the second light sources 111 and 112 toward the target object, and each of the first and the second wavelength controllers 121 and 122 may be directly installed on one side of each light source. Each of the first and the second wavelength controllers 121 and 122 may adjust the peak wavelength of corresponding one of the first and the second light sources 111 and 112 under the control of the controller 140.

For example, the first and the second wavelength controllers 121 and 122 may be configured as temperature control members, for example, resistance heating elements or thermoelectric elements, which control the peak wavelength by adjusting the temperature of each of the first and the second light sources 111 and 112, but are not limited thereto, and various members capable of adjusting an emission wavelength band of the light source may be utilized.

After the light is emitted from the first and the second light sources 111 and 112 toward a target object, the light is reflected from or scattered by the target object. The reflected or the scattered light is received, e.g., detected, by the detection unit 130. The reflection or the scattering of the light from the target object is based on the tissue characteristic of the target object. The detection unit 130 may include a photodiode (PD), convert the detected optical signal into an electrical signal and transmit the electrical signal to the controller 140. In this case, the detection unit 130 may include a photodiode array in which a plurality of photodiodes are arranged.

The controller 140 generates a control signal to control the light source unit 110 to emit light to the target object. The controller 140 may set a peak wavelength emitted from each of the first and the second light sources 111 and 112 before operating each of the first and the second light sources 111 and 112. In this case, the controller 140 may set a peak wavelength of each of the first and the second light sources 111 and 112 by individually controlling the first and the second wavelength controllers 121 and 122 that correspond to the respective first and second light sources 111 and 112. The first and the second wavelength controllers 121 and 122 may be temperature control members to control the peak wavelengths by adjusting the temperatures of the corresponding first and second light sources 111 and 112.

When the peak wavelengths to be emitted from the first and the second light sources 111 and 112 are set, the controller 140 may turn on the first and the second light sources 111 and 112 to emit light. In this case, the controller 140 may operate the first and the second light sources 111 and 112 in a time-division manner in which the first and the second light sources 111 and 112 are sequentially controlled to be on or off, but the aspects of the present disclosure are not limited thereto, such that the controller 140 may simultaneously turn on the first and the second light sources 111 and 112 to emit light at the same time. In addition, the controller 140 may turn on all or some of the first and the second light sources 111 and 112. Alternatively, the controller 140 may classify the first and the second light sources 111 and 112 into two or more groups according to a predetermined peak wavelength, and control the groups of the light sources in a time-division manner. However, these are merely examples, and the method of controlling the light sources may be adjusted based on a variety of information, such as the battery state, the application field of the spectrometer, and the size of a photodiode array to detect light.

In this case, a condition for operating a light source, which includes emission time, an order of operation, a current intensity, and pulse duration, may be set for each light source in advance, and the controller 140 may control the operating method for the light sources by referencing the preset light source operation condition. In addition, by operating the light sources according to the current intensity and pulse duration of each light source to be operated, it is possible to shift the set peak wavelength of each light source to another wavelength band according to the temperature control. By doing so, the peak wavelengths of the first and the second light sources 111 and 112 may be set at fine intervals.

When the first and the second light sources 111 and 112 emit light toward the target object and the detection unit 130 detects light received from the target object, the controller 140 may receive a signal detected from the detection unit 130 and reconstruct a spectrum required for analysis using the received signal.

Figure 2:
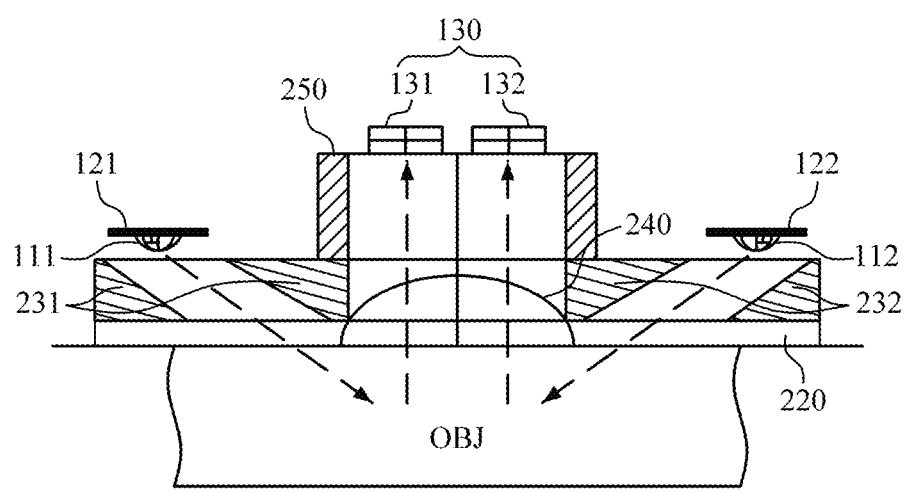
FIG. 2 is a diagram illustrating a configuration of a spectrometer according to one exemplary embodiment.
Figure 3:
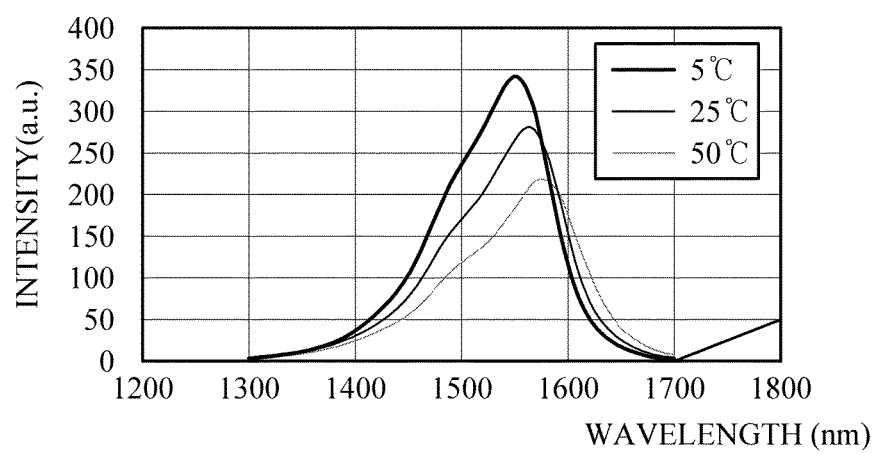
FIG. 3 is a graph for describing a change in peak wavelength according to a temperature.

FIG. 2 is a diagram illustrating a configuration of a spectrometer according to one exemplary embodiment. FIG. 3 is a graph for describing a change in peak wavelength according to temperature.

The spectrometer 100 and the spectrum reconstruction according to one exemplary embodiment will be described in detail with reference to FIGS. 1 to 3.

Referring to FIGS. 1 and 2, the spectrometer 100 includes the first and the second light sources 111 and 112 and a first detector 131 and a second detector 132 of the detection unit 130 are disposed. In this case, it is illustrated that the first and the second light sources 111 and 112 and first and the second detectors 131 and 132 are provided, but this is merely an example for convenience of description, and the numbers of the light sources and the detectors are not particularly limited.

In addition, the spectrometer 100 may include a cover formed on the lower part in contact with the target object OBJ and the cover 220 may be formed of anti-reflection (AR) coated glass.

Also, the spectrometer 100 may further include a redirecting optical system comprising a first redirecting element 231 and a second redirecting element 232, and a conical part of a first converging cylinder 250, which altogether form an optical path changing the radiation direction so as to provide uniform illumination of the desired region of the target object OBJ. In this case, the first and the second redirecting elements 231 and 232 may control the directions of the light emitted from the first and the second light sources 111 and 112 so as to direct the part of the target object OBJ to be examined, for example, a radial artery, or the venous blood or capillary blood of the upper part of the wrists. The first and the second redirecting elements may be made of reflective material such as optical mirrors. However, the first and the second redirection elements 231 and 232 are not limited to the above description, and may be configured to automatically adjust the directions or angles thereof under the control of the controller 140.

The light emitted from the first and the second light sources 111 and 112 may enter the target object OBJ along optical paths as represented by arrows, and be scattered or reflected according to the tissue characteristic of the target object OBJ and travel toward the detection unit 130. Each of the first and the second detectors 131 and 132 detects the light received from the target object OBJ. In this case, the spectrometer 100 may further include a light concentrator 240 to concentrate the light reflected or scattered from the target object OBJ to direct to the director 130. The light concentrator 240 may be configured as an optical module, such as an optical lens.

In addition, each of the first and the second wavelength controllers 121 and 122 may be directly installed on one surface of corresponding one of the first and the second light sources 111 and 112. At this time, each of the first and the second wavelength controllers 121 and 122 may be detachably installed on the corresponding first and second light sources 111 and 112 or may be installed integrally with the corresponding first and second light sources 111 and 112. In this case, the first and the second wavelength controllers 121 and 122 may be configured as temperature control members, for example, resistance heating elements or thermoelectric elements which control the temperatures of the first and the second light sources 111 and 121.

The controller 140 may be electrically connected with the first and the second wavelength controllers 121 and 122 and the light sources 111 and 112. The controller 140 may control the temperature of each of the first and the second wavelength controllers 121 and 122 so that the first and the second light sources 111 and 112 to be operated can emit light of a preset peak wavelength band.

For example, FIG. 3 shows a change in wavelength emitted according to a temperature of the light source, for example, LED, and it is seen that the peak wavelength of light emitted increases as the temperature rises. Therefore, the light source operating condition including the peak wavelength to be emitted and the temperature for emitting each peak wavelength may be defined in advance for each of the first and the second light sources 111 and 112. For example, the first light source 111 may be set to emit a peak wavelength of about 1550 nm, and accordingly, a set temperature of the first wavelength controller 121 may be set to be 5° C. In addition, the second light source 112 may be set to emit a peak wavelength of about 1580 nm, and accordingly, a set temperature of the second wavelength controller 122 may be set to be 50° C.

In this case, the light source operating condition may be adjusted according to a command from a user. The user may input various operating conditions including the set temperatures of the first and the second wavelength controllers 121 and 122 through an interface, and at this time, the controller 140 may change the set temperatures of the first and the second wavelength controllers 121 and 122 and other operating conditions based on the information input by the user.

The light source operating condition may be defined in advance according to various conditions, such as the utilization purpose and application field of the spectrometer, the accuracy of analysis, and the number of flight sources. For example, in the case of biometric information measurement, the wavelength band of light to be emitted may be determined according to a type of biometric information to be measured, and accordingly, an appropriate temperature may be set. In addition, when many light sources are integrated in the spectrometer, the temperature may be finely set to detect light having close peak wavelengths.

In addition, the light source operating condition may be stored in a storage module inside a device in which the spectrometer 100 is mounted or in a separate external storage device interlocked with the device. In this case, the storage device may include a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, but is not limited thereto.

In addition to the set temperatures of the first and the second wavelength controllers 121 and 122 for controlling the peak wavelengths of the first and the second light sources 111 and 112, the light source operating condition may further include operation duration and order of operation of the first and the second light sources 111 and 112, current intensity, and pulse duration.

When the temperature of each of the first and the second light sources 111 and 112 is adjusted to control the peak wavelength of corresponding one of the first and the second light sources 111 and 112, the controller 140 may control the light sources to emit light by turning on or off the light sources in a time division manner based on the information about the order of operation and pulse duration of each of the first and the second light sources 111 and 112. At this time, in the case of operating the light sources in a time-division manner, the order of operation may be defined according to the arrangement order of the array of the first and the second light sources 111 and 112 or the order of the intensity of the wavelength band to be emitted. In addition, the controller 140 may shift the peak wavelength of each of the first and the second light sources 111 and 112 to another wavelength band by adjusting the current of corresponding one of the first and the second light sources 111 and 112 based on the set current intensity information of corresponding one of the first and the second light sources 111 and 112.

FIGS. 4A to 4D are diagrams for describing a spectrum reconstruction process in the spectrometer. FIG. 5 is a graph for describing a spectrum reconstruction performance of the spectrometer according to one exemplary embodiment.

Figure 4A:
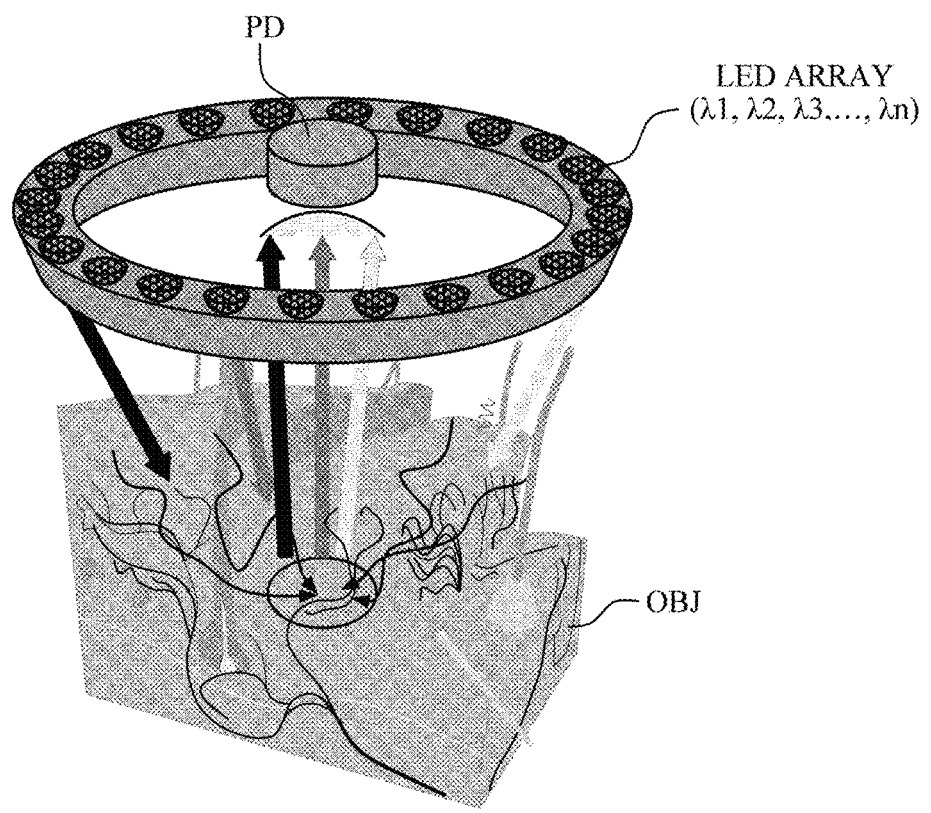
FIGS. 4A to 4D are diagrams for describing a spectrum reconstruction process in the spectrometer.
Figure 4B:
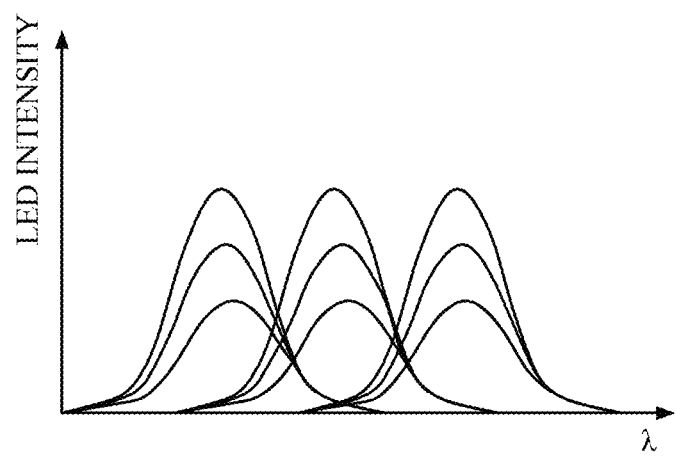
Figure 5:
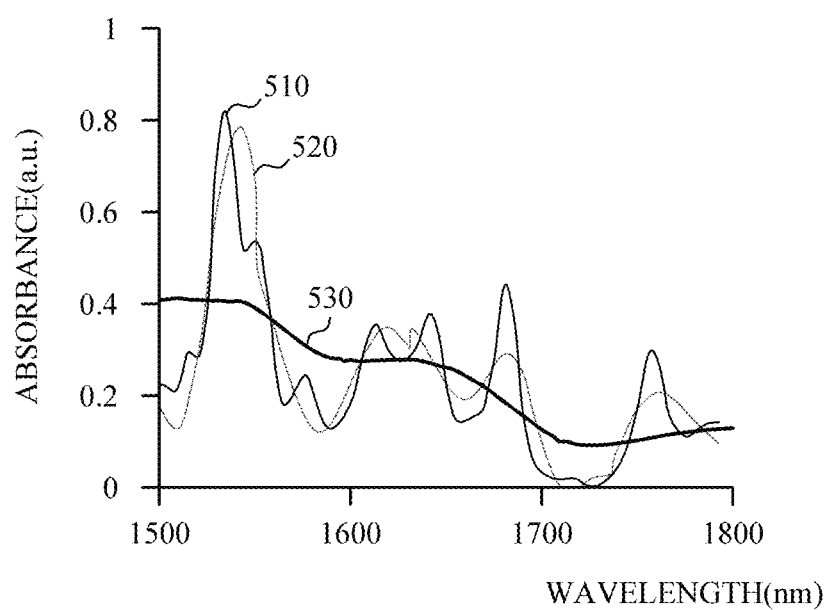
FIG. 5 is a graph for describing a spectrum reconstruction performance of the spectrometer according to one exemplary embodiment.

Referring to FIGS. 4A and 4B, a light source unit includes an LED array consisting of n number of LEDs, and peak wavelengths of each of the LEDs are set to be $\lambda_1$, $\lambda_2$, $\lambda_3$, . . . , and $\lambda_n$ according to a light source operating condition, such as a temperature, a current intensity, and pulse duration. For example, even when a part of the light source is set to have the same temperature, the peak wavelength may be shifted to another wavelength by finely adjusting the current intensity or the pulse duration, thereby allowing the light source to have a different peak wavelength.

Figure 4C:
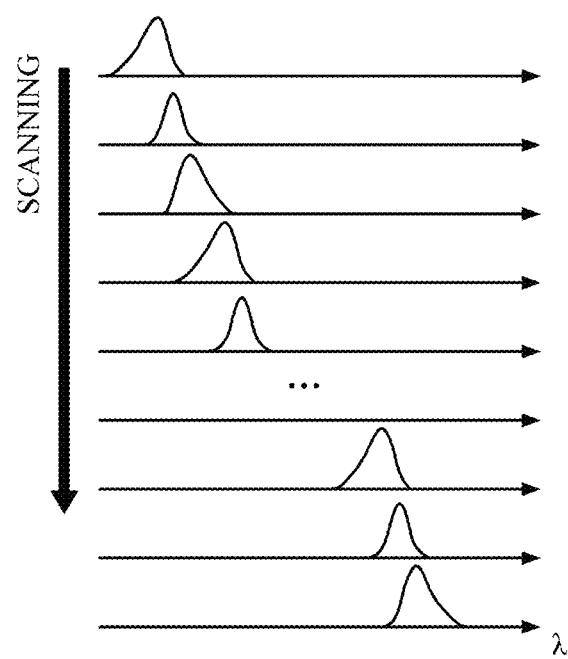

Referring to FIG. 4C, a controller may sequentially operate each of the light sources to emit light based on the set order of operation and pulse duration, and a detector photodiode (PD) detects light received from a target object OBJ. At this time, only some of the light sources may be operated or the light sources may be classified into groups and the groups may be operated in a time-division manner.

Figure 4D:
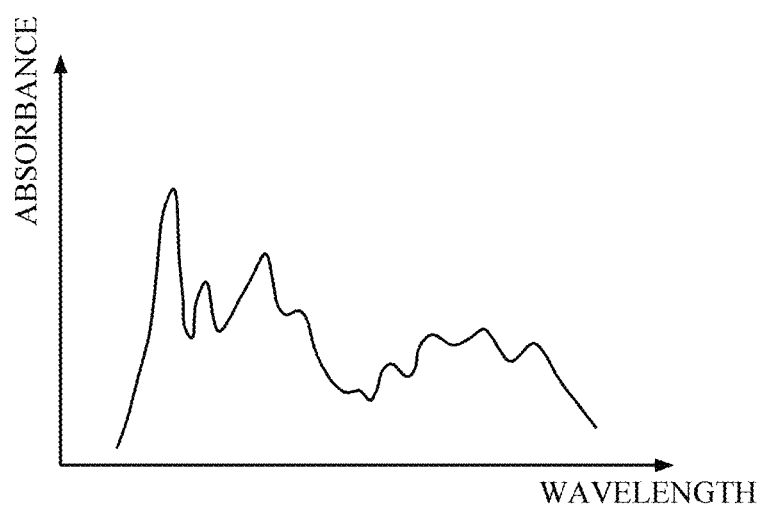

Referring to FIG. 4D, the controller may receive an optical signal detected by the detector PD and reconstruct a spectrum. In this case, the controller may reconstruct the spectrum using a Tikhonov regularization method $|_{[JHS1]}$ through the following Equation 1 and Equation 2.

$$Az = U \qquad \text{EQN. (1)}$$

Here, A represents a matrix of a reference spectrum characteristic measured according to an operating condition for each light source, and U represents a matrix of an actual value measured by the detector according to an operating condition identically set for each light source. In addition, z represents a reconstructed spectrum.

$$(\alpha E + A^T A) Z_\alpha = A^T u$$

$$Z_\alpha = (\alpha E + A^T A)^{-1} A^T u \qquad \text{EQN. (2)}$$

Here, u represents each component of U which is a matrix actually measured by the detector, E represents a unit matrix, and A represents a kernel matrix, which is a matrix of a reference spectrum measured according to an operating condition for each light source. In addition, α represents the unit of noise removal.

FIG. 5 shows a reference spectrum 510, a spectrum reconstructed according to one exemplary embodiment, and a spectrum 530 reconstructed in a general way. As shown in FIG. 5, when a spectrum is reconstructed by a method in which a peak wavelength of each light source is adjusted according to the present exemplary embodiment, a spectrum similar to the reference spectrum is obtained. As such, according to the present exemplary embodiment, the wavelength emitted from each of the light sources is adjusted by controlling the temperature of each light source so that a plurality of light sources having different peak wavelengths can be integrated in one spectrometer. In addition, even for the light sources set to have the same temperature, operating conditions for various light sources, such as current intensities or pulse durations, may be set in detail so that the wavelength range between the peak wavelengths of the light sources can be finely adjusted, thereby allowing for accurate spectrum reconstruction.

Figure 6:
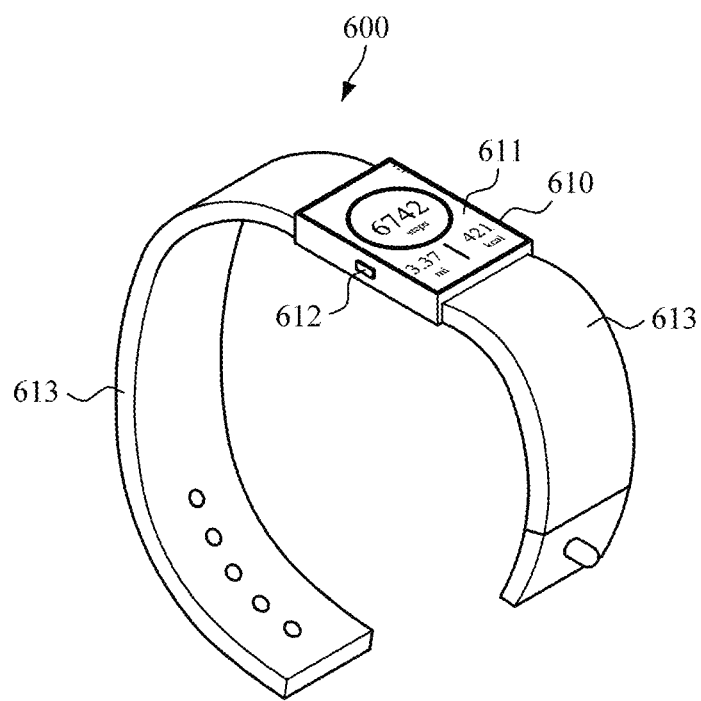
FIG. 6 is a diagram illustrating an apparatus for measuring biometric information according to one exemplary embodiment.
Figure 7:
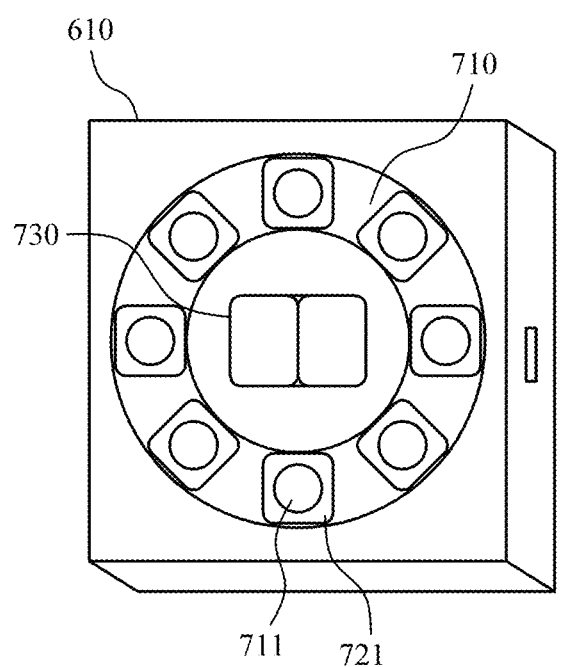
FIG. 7 is a diagram illustrating a rear surface of a main body of the apparatus for measuring biometric information according to one exemplary embodiment.
Figure 8:
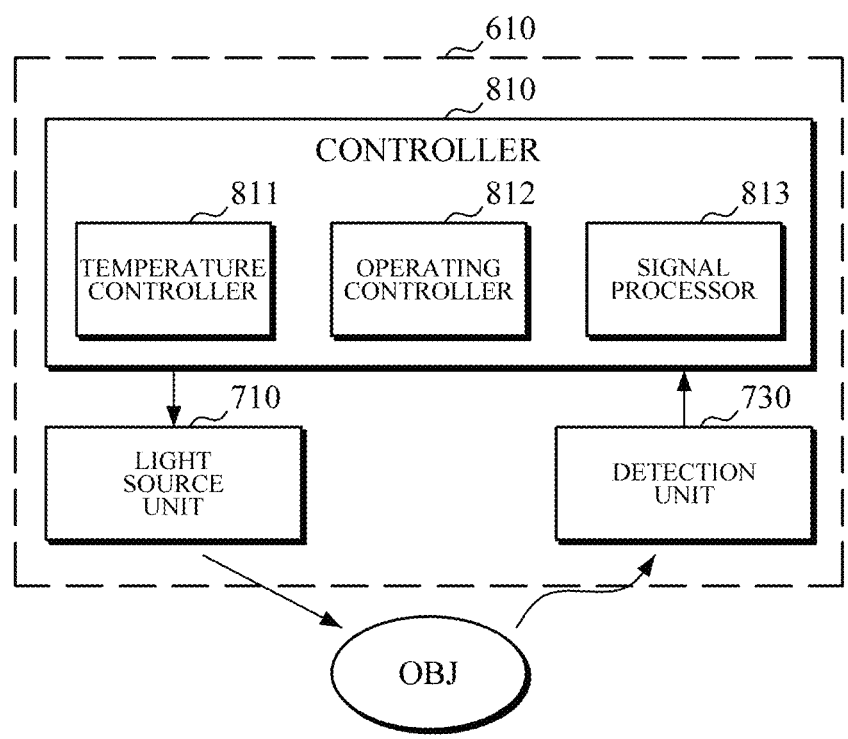
FIG. 8 is a block diagram illustrating a configuration of the main body of the apparatus for measuring biometric information according to one exemplary embodiment.

FIG. 6 is a diagram illustrating an apparatus for measuring biometric information according to one exemplary embodiment. FIG. 7 is a diagram illustrating a rear surface of a main body of the apparatus for measuring biometric information according to one exemplary embodiment. FIG. 8 is a block diagram illustrating a configuration of the main body of the apparatus for measuring biometric information according to one exemplary embodiment.

Exemplary embodiments of the apparatus for measuring biometric information which includes the above-described spectrometer 100 will be described with reference to FIGS. 6 and 8. The apparatus 600 for measuring biometric information according to the present exemplary embodiment may be manufactured in the form of a wristwatch-type wearable device. However, the type of the wearable device is not limited to the above, and the wearable device may include various types of wearable devices, such as a wristwatch type, a wristband type, a ring type, a glass-type, a hairband-type, a chest strap-type, leg strap-type, arm band-type, adhesive bandage or dressing-type, patch-type, and the like. Also, the shape or size of the wearable device is not particularly limited.

Referring to FIGS. 6 to 8, the apparatus 600 includes a main body 610 and a strap 613.

The main body 610 is worn on a wrist of a target object with the strap 613, and the main body 610 may be configured to perform biometric information measurement and various functions. The main body 610 may also be worn over other parts of the body, including, but not limited to, the chest, the lower arm, the upper arm, legs, etc.

The strap 613 may be formed of flexible members connected to each end of the main body 610 and coupled to each other so as to wrap around the wrist in a state in which the main body 610 is in close contact with the wrist, e.g., in direct contact. In this case, a battery for supplying power to the wearable device may be embedded in the main body 610 or the strap 613.

The apparatus 600 may further include a spectrometer configuration mounted in the main body 610. The spectrometer configuration may include a light source unit 710, a detection unit 730, and a controller 810. The spectrometer configuration may be detachably or integrally mounted in the main body 610.

The light source unit 710 may be mounted on the rear surface of the main body 610 contacting the wrist when the main body 610 is brought into close contact with the wrist by the strap 613, as shown in FIG. 7. In this case, the light source unit 710 may be an array of a plurality of light sources 711 which are controlled by a plurality of wavelength controllers 721 to emit light of various wavelengths. Each of the plurality of light sources 711 may be exposed to the wrist or disposed close to the wrist so as to easily irradiate light to the wrist, and each of the plurality of wavelength controllers 721 for controlling the temperature of each of the plurality of light sources 711 may be directly attached to the rear surface of each of the plurality of light sources 711. Although FIG. 7 illustrates that the plurality of light sources 711 is arranged or arrayed in a circular manner, it is merely an example, and the array may be arranged in various manners according to the shape of the main body, the number of light sources, or the like.

In addition, the light source unit 710 may further include a redirecting element to adjust the direction or angle of each light source so that the light source can irradiate light to the part of a target object OBJ to be examined.

The detection unit 730 is mounted in the main body 610, and when the light source 711 emits light to the wrist under the control of the controller 810 in a state in which the main body 610 is worn on the wrist, the detection unit 730 detects light scattered or reflected from the skin tissue. In this case, the detection unit 730 may include an array of a plurality of photodiodes.

The controller 810 receives a command from a user and performs an operation in response to the received command. In this case, when the user inputs a biometric information measurement command, the controller 810 may control the light source unit 710 and the detection unit 730 to acquire an optical signal and may detect the biometric information using the acquired optical signal.

The controller 810 may include a temperature controller 811, an operating controller 812, and a signal processor 813, as shown in FIG. 8.

When the biometric information measurement command is received from the user, the temperature controller 811 may set a temperature of each of the plurality of light sources 711 by controlling the corresponding one of the plurality of wavelength controllers 721 so that the plurality of light sources 711 of the light source unit 710 emit light of preset wavelengths.

When the temperature of each of the plurality of light sources 711 is set, the operating controller 812 turns on each of the plurality of light sources 711 to emit light to the wrist, which is the target object OBJ. In this case, the operating controller 810 may check a light source operating condition and operate the plurality of light sources 711 based on the information about the light sources to be operated, an order of operating the light sources, and current intensity, and pulse duration.

For example, the operating controller 812 may operate all or some of the light sources according to the preset light source operating condition, and or may control the light sources to emit light by turning on the light sources simultaneously or in a time-division manner. As such, an emission wavelength band which has been set for each light source through the temperature control of the temperature controller 811 may be adjusted by controlling the current intensity or pulse duration of each light source.

In addition, the operating controller 812 may control a redirecting element of the light source unit 710 when needed so that light is directed toward the part of the target object to be examined. In this case, the light source operating condition may further include information about a direction or angle of the redirecting element predefined according to the part of the target object to be examined or the user's characteristic.

The signal processor 813 receives a command input by the user and generates a control signal for processing the received command. For example, when the user inputs a biometric information measurement command and a control command for a basic function of the apparatus 600, such as a time-related function, a multimedia function, such as music, a function for communication connection with an external device, and the like, through the touch input via an operation unit 612 or a display 611, the signal processor 813 receives and processes the command.

In addition, when the light source unit 710 emits light to the target object OBJ and the detection unit 730 detects received light scattered or reflected from the target object OBJ, the signal processor 813 may receive an optical signal from the detection unit 730 and detect biometric information. Here, the biometric information may include a blood glucose level, triglycerides, cholesterol, calories, protein, and uric acid.

Moreover, the signal processor 813 may reconstruct a spectrum based on the optical signal received from the detection unit 730 and detect the biometric information based on the reconstructed spectrum. At this time, the signal processor 813 may reconstruct the spectrum using a Tikhonov regularization method as shown in Equation 1 and Equation 2 described above.

Further, the signal processor 813 may generate an alarm signal or warning information based on the measured biometric information and information of the user, such as age, sex, disease, and the like, and provide a variety of information to the user through the display 611. Also, when a haptic device is mounted in or connected to the apparatus 600, risk information or warning information through tactile sensation or vibration. However, aspects of the present disclosure are not limited to the above examples, and the information may be provided to the user by combining two or more visual and non-visual methods according to the type of an interface module, the performance of the device, and the purpose of provision of information.

The display 611 may be mounted on the upper part (opposite to the wrist) of the main body 610 so as to be exposed to the outside. The display 611 may display a result of measuring the biometric information, interface information for an interaction with the user, and the like. In this case, the display 611 may display the result of measuring the biometric information, alarm, and warning information to the user by applying various visual schemes, such as colors, and types and thicknesses of lines. In addition, the display 611 may be configured as a module capable of touch input, receive a command input by the user through a touch input, and transmit the received command to the signal processor 813.

In addition, the apparatus 600 may further include the operation unit 612 mounted in the main body 610, and at this time, the operation unit 612 may be formed on one surface of the main body 610 to be exposed to the outside, receive various control commands input by the user, and transmit the commands to the controller.

Moreover, although not illustrated, a communicator may be additionally installed in the main body 610, and may be communicatively connected with another external device using a communication technology. The communicator may transmit the measured biometric information to another external device under the control of the signal processor 813 so that the external device can perform various functions related to healthcare monitoring using biometric information. For example, the external device may generate statistical information by managing the history of biometric information of the user and display the generated statistical information on the display in the form of a graph or the like. At this time, the external device may be an information processing device, such as a smartphone, a tablet PC, a desktop PC, a notebook PC, or the like, which has superior computing performance relative to the apparatus 600.

In this case, the communication technology may include Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, ANT+ communication, Wi-Fi communication, mobile communication, or the like, but is not limited thereto.

Figure 9:
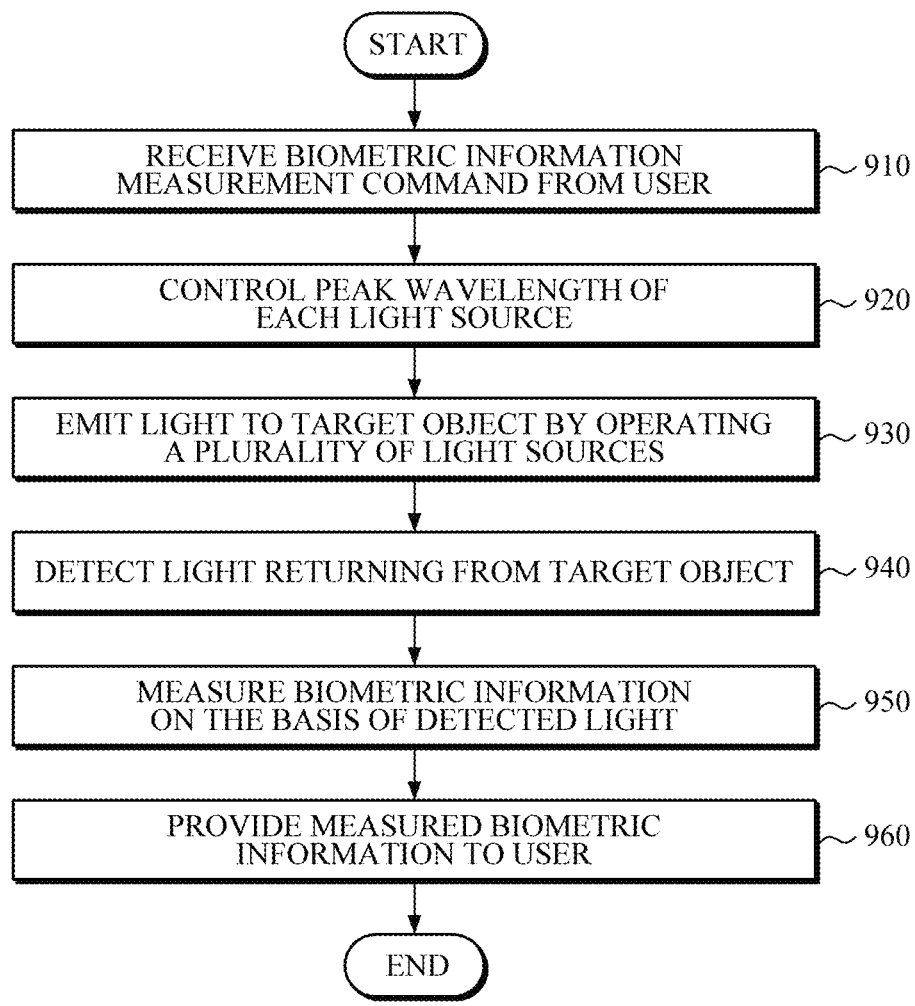
FIG. 9 is a flowchart illustrating a method of measuring biometric information according to one exemplary embodiment.

FIG. 9 is a flowchart illustrating a method of measuring biometric information according to one exemplary embodiment. The method of FIG. 9 may be performed by the apparatus 600 for measuring biometric information according to one exemplary embodiment.

Referring to FIG. 9, the apparatus 600 for measuring biometric information receives a biometric information measurement command from a user, as depicted in 910. At this time, the user may input various commands through interaction with the apparatus 600 via an interface module mounted in the apparatus 600.

Thereafter, when a biometric information measurement command has been received, the apparatus 600 controls the peak wavelength of each of the plurality of light sources, as depicted in 920. For example, the apparatus 600 may control the peak wavelength emitted by each light source by adjusting the temperature of each light source based on a preset light source operating condition. In this case, when only some light sources are set to be operated, it is possible to adjust the temperatures of the relevant light sources. In order to adjust the temperature of the light source, a temperature control member, such as a resistance heating element or a thermoelectric element, may be installed on one side of each light source, and the temperatures of the light sources may be adjusted through the temperature control members.

Thereafter, when the temperature setting for the light sources to be operated is complete, the apparatus 600 controls the light sources to emit light of set wavelength bands by turning on the light sources simultaneously or in a time-division manner based on the light source operating condition, such as the light sources to be operated, operation duration, order of operation, current intensity, and pulse duration, as depicted in 930.

When light emitted from the light sources is scattered or reflected from the target object and the apparatus 600 detects the scattered or reflected light, as depicted in 940.

Then, the apparatus 600 measures biometric information based on the detected optical signal, as depicted in 950. In this case, the apparatus 600 may reconstruct a spectrum based on the detected light of various peak wavelength bands and measure the biometric information using the reconstructed spectrum.

Thereafter, a variety of information including the measured biometric information is provided to the user, as depicted in 960. At this time, the information, such as biometric information and warning and/or alarm, may be displayed using various visual methods, and may be provided through vibration or tactile sensation using a haptic device.

The current exemplary embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A spectrometer comprising:
   a plurality of light sources configured to emit light toward a target object;
   a plurality of wavelength controllers disposed on surfaces of the plurality of light sources and configured to adjust peak wavelength bands of the plurality of light sources so that the peak wavelength bands of the plurality of light sources are different from each other;
   a detector disposed at a center of the plurality of light sources having a circular arrangement and configured to detect the light when the light is scattered or reflected from the target object; and
   a spectrometer controller configured to:
      perform a temperature-based wavelength adjustment by setting a temperature of each of the plurality of light sources, and perform a pulse-duration-based wavelength adjustment by setting a pulse duration of each of the plurality of light sources after performing the temperature-based wavelength adjustment, to adjust the peak wavelength bands of the plurality of light sources based on the temperature-based wavelength adjustment and the pulse-duration-based wavelength adjustment,
      sequentially turn on and off the plurality of light sources in an order of the circular arrangement of the plurality of light sources, so that a peak wavelength band of the light emitted from the plurality of light sources continuously changes over time while the detector is detecting the light, and
      reconstruct a spectrum based on the light that is emitted from the plurality of light sources and then is detected by the detector,
      wherein a matrix that represents a reference spectrum characteristic of an operating condition of each of the plurality of light sources is set based on the temperature-based wavelength adjustment and the pulse-duration-based wavelength adjustment.

2. The spectrometer of claim 1, wherein one of the plurality of wavelength controllers comprises at least one from among a resistance heating element and a thermoelectric element to adjust the temperature of each of the plurality of light sources.

3. The spectrometer of claim 1, wherein the plurality of light sources are arranged to surround the detector.

4. The spectrometer of claim 1, further comprising:
   a plurality of redirection elements that comprise a refractive material, and are disposed between a bottom cover of the plurality of light sources and the detector; and
   wherein the plurality of redirection elements form a plurality of slant optical paths that extend in different directions toward a same target location, and the plurality of light sources are disposed above the plurality of redirection elements, respectively.

5. An apparatus for measuring biometric information, the apparatus comprising:
   a main body;
   a light source unit disposed in the main body and comprising
      a plurality of light sources configured to emit light toward a target object, and a plurality of wavelength controllers disposed on the plurality of light sources and configured to adjust peak wavelength bands of the plurality of light sources so that the peak wavelength bands of the plurality of light sources are different from each other;

a detector disposed at a center of the plurality of light sources having a circular arrangement and configured to detect the light when the light is scattered or reflected from the target object; and a spectrometer controller disposed in the main body and configured to:

perform a temperature-based wavelength adjustment by setting a temperature of each of the plurality of light sources, and perform a pulse-duration-based wavelength adjustment by setting a pulse duration of each of the plurality of light sources after performing the temperature-based wavelength adjustment, to adjust the peak wavelength bands of the plurality of light sources based on the temperature-based wavelength adjustment and the pulse-duration-based wavelength adjustment, and sequentially turn on and turn off the plurality of light sources in an order of the circular arrangement of the plurality of light sources, so that a peak wavelength band of the light emitted from the plurality of light sources continuously changes over time while the detector is detecting the light, and to measure the biometric information of the target object based on the detected light, and reconstruct a spectrum based on the light that is emitted from the plurality of light sources and then is detected by the detector, wherein a matrix that represents a reference spectrum characteristic of an operating condition of each of the plurality of light sources is set based on the temperature-based wavelength adjustment and the pulse-duration-based wavelength adjustment.

6. The apparatus of claim 5, wherein one of the plurality of wavelength controllers comprises at least one from among a resistance heating element and a thermoelectric element to adjust the temperature of one of plurality of light sources.

7. The apparatus of claim 5, wherein the spectrometer controller comprises a signal processor configured to detect an optical signal detected by the detector and measure the biometric information by processing the received optical signal.

8. The apparatus of claim 7, wherein the signal processor reconstructs a spectrum based on the received optical signal and measures the biometric information based on the reconstructed spectrum.

9. The apparatus of claim 5, further comprising:

a plurality of redirection elements that comprise a refractive material, and are disposed between a bottom cover of the spectrometer and the detector; and wherein the plurality of redirection elements form a plurality of slant optical paths that extend in different directions toward a same target location, and the plurality of light sources are disposed above the plurality of redirection elements, respectively.

10. The apparatus of claim 5, wherein the biometric information comprises at least one from among blood glucose level, triglycerides information, cholesterol information, caloric information, protein information, and uric acid information.

11. The apparatus of claim 5, wherein the light source unit further comprises a plurality of redirecting elements to adjust a direction of the light emitted from the plurality of light sources to be directed toward the target object.

12. The apparatus of claim 5, further comprising a display configured to display a number of pieces of information including the measured biometric information under a control of the spectrometer controller.

13. The apparatus of claim 5, further comprising a communicator configured to be communicatively connected to an external device under a control of the spectrometer controller and transmit a number of pieces of information including the measured biometric information.

14. A method of measuring biometric information, the method comprising:

receiving a biometric information measurement command from a user;

controlling a plurality of wavelength controllers corresponding to a plurality of light sources to adjust peak wavelengths of the plurality of light sources so that the peak wavelength bands of the plurality of light sources are different from each other;

operating the plurality of light sources to emit light toward a target object;

detecting the light when the light reflected or scattered from the target object using a detector that is disposed at a center of the plurality of light sources having a circular arrangement; and measuring biometric information of the target object based on the detected light, wherein the operating the plurality of light sources comprises:

performing a temperature-based wavelength adjustment by setting a temperature of each of the plurality of light sources, and performing a pulse-duration-based wavelength adjustment by setting a pulse duration of each of the plurality of light sources after performing the temperature-based wavelength adjustment, to adjust the peak wavelength bands of the plurality of light sources based on the temperature-based wavelength adjustment and the pulse-duration-based wavelength adjustment, and sequentially turning on and off the plurality of light sources in an order of the circular arrangement of the plurality of light sources, so that a peak wavelength band of the light emitted from the plurality of light sources continuously changes over time while the detector is detecting the light, and reconstructing a spectrum based on the light that is emitted from the plurality of light sources and then is detected by the detector, wherein a matrix that represents a reference spectrum characteristic of an operating condition of each of the plurality of light sources is set based on the temperature-based wavelength adjustment and the pulse-duration-based wavelength adjustment.

15. The method of claim 14, wherein the measuring of the biometric information comprises reconstructing a spectrum based on the detected light and measuring the biometric information based on the reconstructed spectrum.

16. The method of claim 14, further comprising displaying the measured biometric information to the user.

17. A spectrometer comprising:

a plurality of light sources configured to emit light toward a target object, each of the plurality of light sources comprising:

a first surface at which the light is emitted toward the target object; and a second surface which is opposite to the first surface;

a plurality of wavelength controllers disposed on second surfaces of the plurality of light sources and configured to adjust temperatures of the plurality of light sources so that peak wavelength bands of the plurality of light sources are different from each other, each of the plurality of wavelength controllers comprising a resistance heating element or a thermoelectric element;

a photodiode detector disposed at a center of the plurality of light sources having a circular arrangement and configured to detect the light when the light is reflected or scattered from the target object; and a spectrometer controller configured to perform a temperature-based wavelength adjustment by setting a temperature of each of the plurality of light sources, and perform a pulse-duration-based wavelength adjustment by setting a pulse duration of each of the plurality of light sources after performing the temperature-based wavelength adjustment, to adjust the peak wavelength bands of the plurality of light sources based on the temperature-based wavelength adjustment and the pulse-duration-based wavelength adjustment, and sequentially turn on and off the plurality of light sources in an order of the circular arrangement of the plurality of light sources, so that a peak wavelength band of the light emitted from the plurality of light sources continuously changes over time while the detector is detecting the light, and reconstruct a spectrum based on the light that is emitted from the plurality of light sources and then is detected by the detector, wherein a matrix that represents a reference spectrum characteristic of an operating condition of each of the plurality of light sources is set based on the temperature-based wavelength adjustment and the pulse-duration-based wavelength adjustment.

\* \* \* \* \*